US010596235B2

(12) United States Patent
Rämsch et al.

(10) Patent No.: US 10,596,235 B2
(45) Date of Patent: Mar. 24, 2020

(54) PHARMACEUTICAL PREPARATION

(71) Applicant: Nordmark Arzneimittel GmbH & Co. KG, Uetersen (DE)

(72) Inventors: Christian Rämsch, Groß Norende (DE); Manfred Kurfürst, Moorrege (DE); Rainer Friedel, Hannover (DE); Olaf Friedrich, Tornesch (DE); Silke Hüttler, Altenmoor (DE)

(73) Assignee: Nordmark Arzneimittel GmbH & Co. KG, Uetersen (DE)

( * ) Notice: Subject to any disclaimer, the term of this patent is extended or adjusted under 35 U.S.C. 154(b) by 39 days.

(21) Appl. No.: 15/182,779

(22) Filed: Jun. 15, 2016

(65) Prior Publication Data

US 2016/0287679 A1 Oct. 6, 2016

Related U.S. Application Data

(63) Continuation of application No. 13/146,653, filed as application No. PCT/EP2009/000566 on Jan. 29, 2009, now abandoned.

(51) Int. Cl.
*C12N 9/20* (2006.01)
*A61K 38/46* (2006.01)

(52) U.S. Cl.
CPC .................................. *A61K 38/465* (2013.01)

(58) Field of Classification Search
None
See application file for complete search history.

(56) References Cited

U.S. PATENT DOCUMENTS

| | | | |
|---|---|---|---|
| 2,189,948 A | 2/1940 | Griffith | |
| 4,280,971 A | 7/1981 | Wischniewski | |
| 5,063,160 A * | 11/1991 | Holmes | C11D 3/38627 435/198 |
| 5,378,462 A | 1/1995 | Boedecker | |
| 5,645,832 A | 7/1997 | Braatz et al. | |
| 5,993,806 A | 11/1999 | Galle | |
| 6,270,723 B1 | 8/2001 | Laugharn | |
| 7,407,342 B2 | 8/2008 | Seidel | |
| 7,830,030 B2 | 11/2010 | Altemark | |
| 8,691,282 B2 | 4/2014 | Moest | |
| 8,999,394 B2 | 4/2015 | Moest | |
| 9,107,966 B2 | 8/2015 | Ramsch | |
| 2001/0046493 A1* | 11/2001 | Margolin | A61K 38/47 424/94.2 |
| 2005/0250817 A1 | 11/2005 | Shlieout | |
| 2006/0121017 A1* | 6/2006 | Margolin | A61K 38/47 424/94.2 |
| 2007/0148152 A1 | 6/2007 | Shlieout | |
| 2007/0290426 A1 | 12/2007 | Trede | |
| 2008/0299185 A1* | 12/2008 | Ortenzi | A61K 9/1617 424/451 |
| 2009/0102195 A1 | 4/2009 | Altemark | |
| 2010/0308596 A1 | 12/2010 | Gawrisch | |
| 2011/0052706 A1 | 3/2011 | Moest | |
| 2011/0268844 A1 | 11/2011 | Ramsch | |
| 2012/0213857 A1 | 8/2012 | Moest | |

FOREIGN PATENT DOCUMENTS

| | | |
|---|---|---|
| EP | 0436110 | 7/1991 |
| EP | 1 486 415 A1 | 12/2004 |
| JP | H08143469 | 4/1996 |
| WO | WO 91/18623 | 12/1992 |
| WO | WO 01/76381 | 10/2001 |
| WO | WO 2005/062370 | 6/2005 |
| WO | WO 2006/044529 A1 | 4/2006 |
| WO | WO 2008/127567 A1 | 10/2008 |
| WO | PCT/EP2009/006216 | 8/2009 |
| WO | PCT/EP2009/000566 | 12/2011 |

OTHER PUBLICATIONS

Suzuki et al., Gastroenterology, vol. 112, pp. 2048-2055 (1997).*
Physical Pharmacy, Physical Chemical Principles in the Pharmaceutical Sciences, 2nd Edition, Chapter 7: Solutions, ed. Marin et al., 1969, pp. 143-145 (plus title pages).
Physicochemical Principles of Pharmacy, Chapter 5 (excerpt), ed. Florence and Attwood, 1981, p. 125 (plus title pages).
Joel D. A. Tyndali et al., "Crystal structure of a thermostable lipase from Bacillus stearothermophilus P1" J. Mol. Biology, vol. 323, No. 5, pp. 859-869 (2002).
Rohit Sharma et.al. "Production, purification, characterization, and applications of lipases", Biotechnology Advances, vol. 19, No. 8, pp. 627-662. (2001).
Sachiko Murakami et al. "Study on the Stabilization of Lipase in Aqueous Solution" vol. 19 , No. 9, pp. 493-497 (1983) (with English Abstract).
Office Action issued in parallel Japanese application 2014-115739, dated May 26, 2015.
Japanese Examination Report, dated Mar. 19, 2013, issued in corresponding Japanese patent application No. 2011-546599.
English translation of Japanese Examination Report, dated Mar. 19, 2013, issued in corresponding Japanese patent application No. 2011-546599.
International Search Report, dated Jan. 14, 2010, issued in PCT/EP2009/000566, 3 pages.
Office Action dated Jan. 11, 2019, in Chinese Patent Application No. 201610271033, filed Jan. 29, 2009 w/attached English translation.

* cited by examiner

*Primary Examiner* — Soren Harward
*Assistant Examiner* — Paul D. Pyla
(74) *Attorney, Agent, or Firm* — Oblon, McClelland, Maier & Neustadt, L.L.P.

(57) ABSTRACT

The pharmaceutical preparation for the treatment of pancreatic insufficiency comprises a liquid administering form of enzymes.

6 Claims, 3 Drawing Sheets

PHARMACEUTICAL PREPARATION

The invention relates to pharmaceutical preparations for the treatment of pancreatic insufficiency, for example mucoviscidosis or other pancreatic illnesses. In particular, this invention relates to liquid pharmaceutical preparations of digestive enzymes which have no coating and which are active in the aggressive environment of stomach and duodenum. Moreover, these liquid pharmaceutical preparations are stable and can be stored at high temperatures.

This application claims priority from PCT/EP2009/000566, filed Jan. 29, 2009, and the entire contents of that prior application are incorporated by reference.

BACKGROUND OF THE INVENTION

Excessive expression or lack of effective enzymes often lead to metabolism or gastro-intestinal illnesses. Imbalance of the lipase level can, for example, cause a multitude of digestion illnesses, including the malabsorption of fat. For patients who suffer from mucoviscidosis, chronic pancreatitis and other pancreatic illnesses, fat malabsorption does occur. Commonly observed consequences of fat malabsorption are abdominal pain, steatorrohoea (fat diarrhoea), lack of essential fat acids, of fat-soluble vitamins (for example A, D, E and K) and general developmental disorders.

The usual procedure for the treatment of illnesses with lipase insufficiency are orally administered lipase enzymes, most products on the base of porcine pancreas which has been unfatted, dried and crushed. The corresponding product consists of several enzymes such as lipase, amylases, proteases, esterases etc.

Generally available administering forms are usually tablets, micro-tablets, micro-dragees, capsules, powder and granules coated with a film resistant to gastric juice. The disadvantage of these administering forms consists in the discomfort of the administering to patients who have to swallow big tablets or capsules. In particular in the case of patients who are not able to swallow tablets such as small children or who need artificial feeding, these administration forms can be applied only with difficulties. The crushing of the tablets cannot assure any homogeneous distribution of the enzymes to the chymus and the low solubility of the product can lead to the occlusion of the feeding tube.

Liquid formulations of digestion enzymes have been described for example in EP 0826375 or US 2006/0128587. In these patent applications the enzymes are stabilized either with additives, or by modification of the enzymes. However, in both cases, the enzyme solutions have to be prepared fresh before administration which is less convenient than a ready-made liquid preparation. Moreover, the effects of additives on the active substance, on the effectiveness and the safety should be considered.

The treatment on the base of easily available pancreatinic preparations has various disadvantages. The lipase is considered as the main enzyme. Because of the low specific lipase activity a quantity of up to 5-10 g per day has to be taken by the patient. Moreover, the porcine lipase is active in a pH range of 5 to 9 and is thus inactive during the passage through the stomach.

Moreover, the lipase activity has to be protected from the acid pH conditions in the stomach because of its sensitivity to a low pH value, for example by a coating of the tablets resistant to gastric juice. In a few medical applications, the accompanying proteolytic or amylolytic enzyme activities are not desired. The amylase content is not desired for children with mucoviscidosis while lipase is therapeutically necessary. Proteases are contraindicated for patients with acute pancreatitis or active phases of chronic pancreatitis (see U.S. Pat. No. 5,645,832). Thus, the availability of a lipase as single protein is advantageous. In U.S. Pat. No. 5,645,832 or U.S. Pat. No. 5,489,530 a lipase obtained from bacteria has already been described in detail. Apart from the making available of a purified single protein, the lipase concentration of bacterial lipase is very high so that only low preparation quantities (approx. 0.2 g) have to be administered. The pH value for the activity of the bacterial lipase is situated between 3 and 9 and thus overcomes the limitations of the stability and activity of porcine lipase/pancreatin. This means that the lipolytic effect of bacterial lipase can be applied with a better effect in the gastrointestinal tract than the products for the therapy of digestion disorders commonly sold on the market. Additionally, the bacterial lipase is a non-animal product which avoids the risk of possible viral infection originating from animal sources.

SUMMARY OF THE INVENTION

This invention provides a liquid pharmaceutical preparation which contains a digestive enzyme. The preparation serves for the treatment of patients with pancreatic insufficiency, for example with mucoviscidosis or other pancreatic illnesses.

It could surprisingly be shown that lipase without coating is active in the aggressive environment of stomach and duodenum and that the enzyme is stable in an aqueous solution over several months at ambient temperature. Additionally, it has been stated that bacterial lipase is able to reduce steatorrohea for mucoviscidosis patients.

DESCRIPTION OF THE INVENTION

Figure 1:
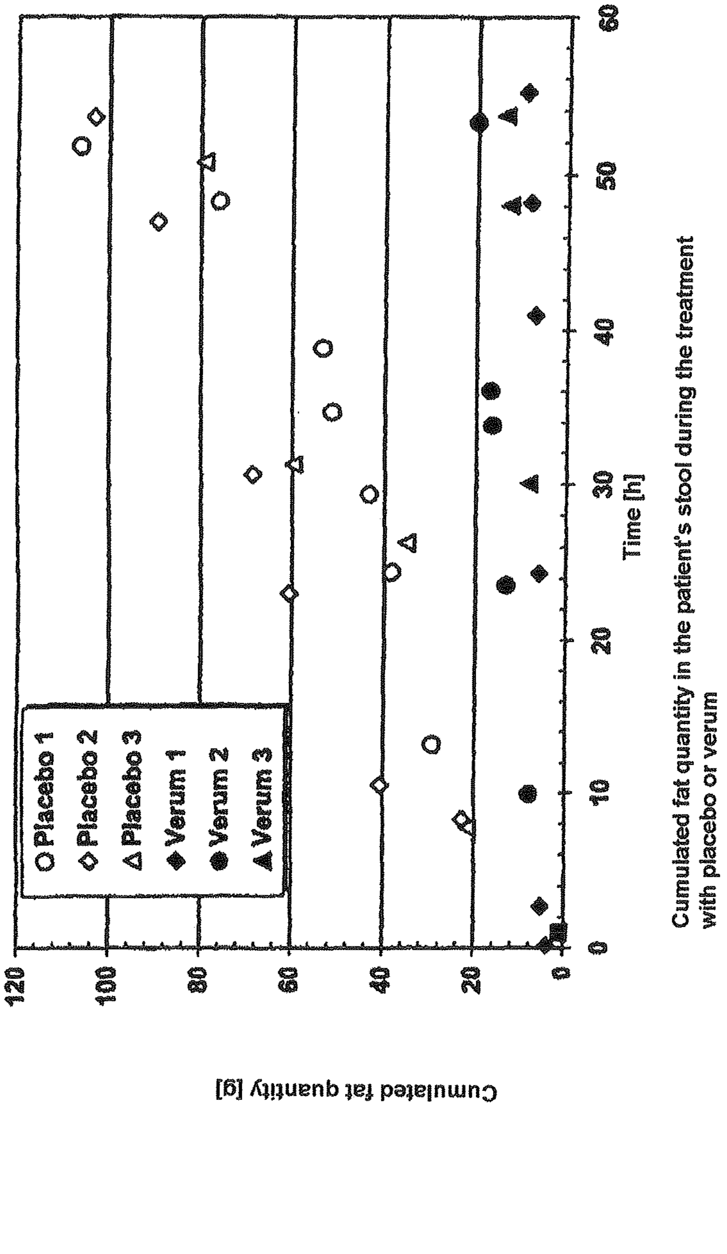
FIG. 1 shows cumulated fat quantity in the patient's stool during the treatment with placebo or verum.

The invention relates to a lipase which is produced in bacteria and its production is expressly described in U.S. Pat. No. 5,645,832.

The lipase application has been proved as an effective treatment of patients who suffer from pancreatitis or mucoviscidosis. The reduction of steatorrohea has been observed during the exclusive application of lipase. No other enzymes such as proteases, amylases or esterases were present (example 1).

Pure bacterial lipase can have specific activities of more than 3.5 milliards U/g. Because of the high lipolytic activity, a lower quantity administered form (i.e. number of tablets or volume of solution) has to be administered to the patients.

This invention offers the lipase as a liquid pharmaceutical preparation in order to overcome the limitations of the usual formulae (tablets) of therapeutic digestion enzymes. In particular in the case of patients who are not able to swallow tablets such as small children, or those who need artificial feeding, the usual administering forms cannot be used or can only be used to a limited extent.

A liquid pharmaceutical product offers the possibility of a convenient dosage of the medicine, homogeneous distribution of the enzyme in the food and use with artificial feeding.

It could be shown that lipase without coating is active under pH conditions which imitate the aggressive environment of the stomach when taking in (example 2). Moreover, it has been shown that the bacterial lipase is stable in an aqueous solution for at least 3 months even at high temperatures (example 3). No chemical modification as it is described in US 2006/0128587 was necessary.

The invention includes formulae which also use stabilizers such as salts
organic acids
amino acids
detergents
sugar
oils
viscosity regulating means.

The matter can be, for the liquid formula, of: solutions, solution/drop; suspensions, suspension drops. The invention is based on the advantages of liquid administering forms, in particular but not exclusively for children.

Liquid administering forms can be prepared either in hat the lipase is produced directly as a liquid solution or by dissolving the active constituent lipase in an aqueous or non aqueous solvent, by suspending the medicine in an appropriate medium or by adding the medicine into one of the two phases of an oil/water system.

Administering forms such as solutions, suspensions and emulsions of lipase are useful for many reasons. They can be formulated for different ways of administering: oral medication, insertion into body cavities or external use. The dosage can be adjusted by dilution and single drops can be administered for example with a dropping device. The liquid oral form can easily be administered to children or patients who are unable to swallow tablets, capsules or any other solid administering form.

The lipase solution is a homogeneous mixture which includes pharmaceutical forms which are designated as water, aromatic water, aqueous acids, solutions.

The lipase suspension refers to a two-phase system which consists of solid lipase which is dispersed in a liquid.

Example 1

Cumulated Fat Quantity in the Patient's Stool During the Treatment with Placebo or Verum—FIG. 1

Bacterial lipase has been tested during a clinical study with mucoviscidosis patients. As shown in FIG. 1 and in the following table with the indication of coefficients of fat absorption of patients under placebo and verum, considerable differences are to be seen in the fat quantity in the stool of the patient under verum as well as the coefficient of fat absorption (CFA). The bacterial lipase significantly improves the resorption of fat during digestion.

| Patient | CFA |
|---|---|
| Placebo 1 | 73.00% |
| Placebo 2 | 64.00% |
| Placebo 3 | 65.00% |
| Verum 1 | 92.00% |
| Verum 2 | 96.00% |
| Verum 3 | 93.00% |

Example 2

Figure 2:
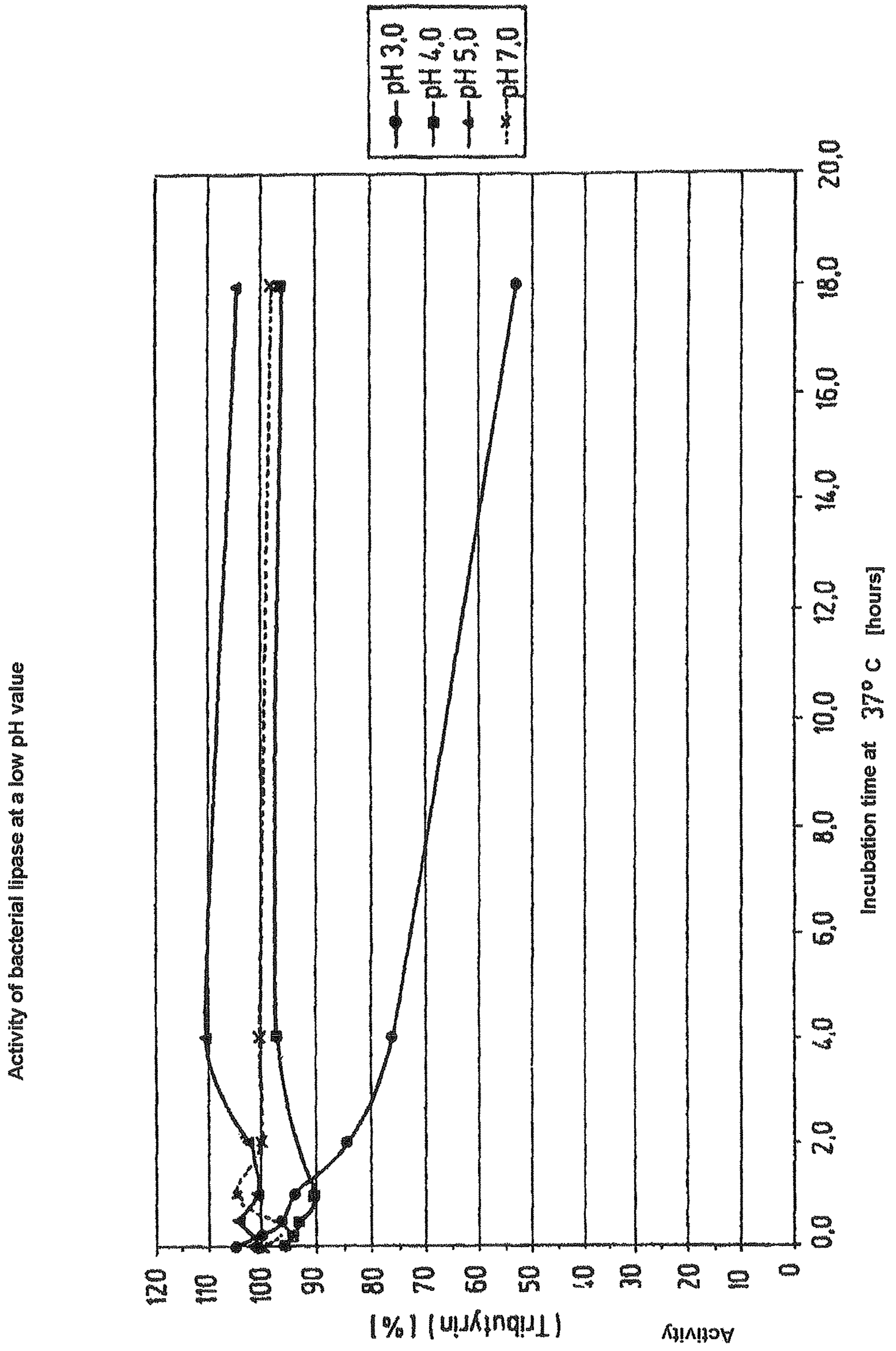
FIG. 2 shows the activity of lipase under conditions of a low pH value (imitation of the pH value in the stomach).

Activity of Lipase Under Conditions of a Low pH Value (Imitation of the pH Value in the Stomach)—FIG. 2

Bacterial lipase has been dissolved and adjusted to the pH value of 1.0, 2.0, 3.0, 4.0 and 5.0. Lipase activities have been measured by applying the tributyrin test after 15, 30 minutes and 1, 2, 4 and 18 hours with the test pH value (8.0).

It has been stated that the pH value increases to pH 4 in the stomach of patients who suffer from mucoviscidosis when swallowing. Bacterial lipase hows under these circumstances a sufficient activity (FIG. 2) while the activity of porcine lipase (made of pancreatin) is reduced by 85% after 2 hours and by 96% after 4 hours at pH 4 (not represented).

Example 3

Figure 3:
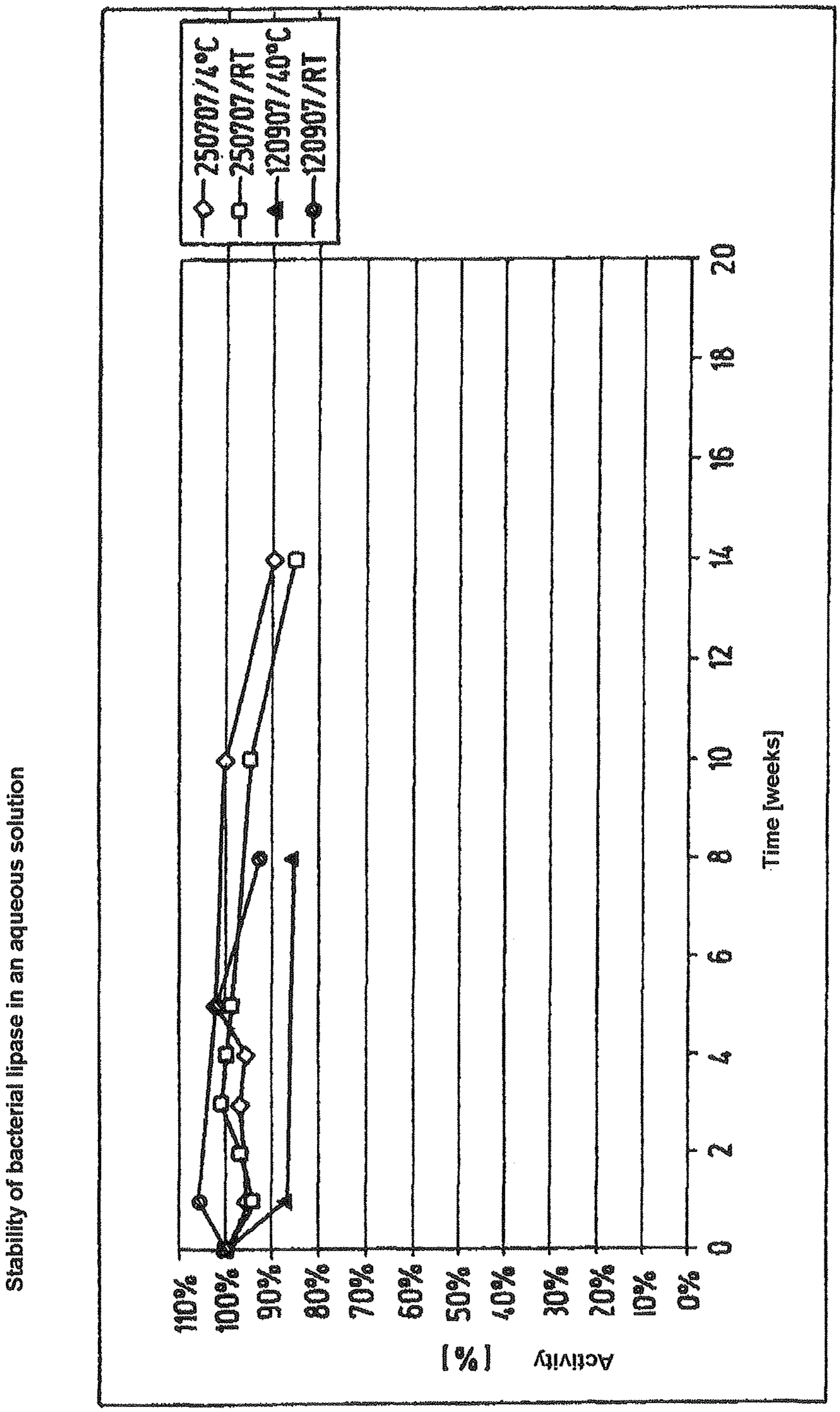
FIG. 3 shows stability of bacterial lipase in an aqueous solution.

Stability of Bacterial Lipase in an Aqueous Solution—FIG. 3

Bacterial lipase has been dissolved in water and incubated at 4° C., ambient temperature and 40° C. The activity has been measured after 1, 2, 3, 4, 5, 10 and 14 weeks. No considerable loss of activity has been stated during this time.

The invention comprises the description with the examples, the claims and the illustrations.

What is claimed:

1. A method for the treatment of pancreatic insufficiency comprising the steps of:

providing a pharmaceutical composition consisting of water and a bacterial lipase, and which has been stored for at least one week, and administering the pharmaceutical composition to a patient suspected of pancreatic insufficiency.

2. The method according to claim 1, wherein the pancreatic insufficiency is mucoviscidosis or pancreatitis.

3. The method according to claim 1, wherein the pharmaceutical composition is prepared by a) direct fabrication of the lipase as liquid solution or b) dissolution of the active constituent lipase in water.

4. The method according to claim 1, whereby the bacterial lipase is selected from the group consisting of the *Burkholderia* type lipase, *Pseudomonas* type lipase, and *Burkholderia plantarii* type lipase.

5. The method of claim 1, wherein the bacterial lipase is active to a pH as low as 3.

6. The method according to claim 1, wherein the bacterial lipase is of the *Burkholderia plantarii* type lipase.

* * * * *